Figure 1:
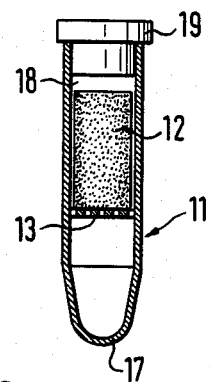

United States Patent [19]

Hebel et al.

[11] Patent Number: 4,774,962

[45] Date of Patent: Oct. 4, 1988

[54] METHOD OF EXTRACTING HUMAN SALIVA

[75] Inventors: Peter Hebel, Wiehl; Rainer Haeckel, Bremen-Borgfeld, both of Fed. Rep. of Germany

[73] Assignee: Walter Sarstedt Kunststoff-Spritzgusswerk, Numbrecht-Rommelsdorf, Fed. Rep. of Germany

[21] Appl. No.: 910,620

[22] Filed: Sep. 23, 1986

[30] Foreign Application Priority Data

Sep. 23, 1985 [DE] Fed. Rep. of Germany ....... 3533888

[51] Int. Cl.$^4$ .............................................. A61B 5/00
[52] U.S. Cl. ..................................... 128/760; 604/317
[58] Field of Search ............... 128/749, 750, 756, 759, 128/760, 762, 767, 768, 769; 604/317, 327, 328, 330, 358; 73/863.21, 863.23; 210/645, 781, 782; 422/72, 272

[56] References Cited

U.S. PATENT DOCUMENTS

| | | | |
|---|---|---|---|
| 3,298,369 | 1/1967 | Pirie | 604/330 |
| 3,688,763 | 9/1972 | Cromarty | 128/769 |
| 3,750,645 | 8/1973 | Bennett et al. | 128/760 |
| 3,864,213 | 2/1975 | Bucalo | 128/749 |
| 3,913,564 | 10/1975 | Freshley | 128/759 |
| 3,958,561 | 5/1976 | Bucalo | 128/762 |
| 4,172,446 | 10/1979 | Bucalo | 128/769 |
| 4,325,388 | 4/1982 | Bucalo | 128/749 |
| 4,379,849 | 4/1983 | Heimreid | 422/72 |
| 4,418,702 | 12/1983 | Brown et al. | 128/760 |
| 4,580,577 | 4/1986 | O'Brien et al. | 128/760 |
| 4,635,488 | 1/1987 | Kremer | 128/760 |

*Primary Examiner*—Max Hindenburg

[57] ABSTRACT

In a method of extracting human saliva a resilient absorbent inert body is chewed by a person and is subsequently introduced into a centrifuge tubule (11) provided with an apertured floor (13). The centrifuge tubule (11) is introduced into a centrifuge and subjected to a spinning process, whereupon the saliva is pressed out of the resilient body (12) and passes through the floor (13) into the lower part of the centrifuge tubule (11).

3 Claims, 1 Drawing Sheet

METHOD OF EXTRACTING HUMAN SALIVA

The invention relates to a method of extracting human saliva in which a chewable, absorbent and resilient inert body is introduced into the mouth and is chewed until the body has sucked itself full of saliva, and wherein the body full of saliva is taken out of the mouth and is placed into a container which has a permeable partition wall at the bottom which is adjoined by a saliva collecting vessel, whereupon forces acting in the direction of the saliva collecting vessel press the saliva out of the resilient body and empty it into the saliva collecting vessel.

Moreover, the invention relates to an apparatus for carrying out this method.

In a known method for extracting human saliva (European Pat. No. 56 241) the resilient bodies which have sucked themselves full of saliva are arranged in a press which has a fluid-permeable partition wall at the bottom which is adjoined by a saliva collecting vessel. The resilient bodies are pressed or squeezed out by screwing a press ram into the container and the saliva which is pressed out is forced through the liquid permeable partition wall and collects in the saliva collecting vessel. After screwing back the press device the saliva which has been presed out can subsequently be passed on for further use.

It is a disadvantge of the known method that the mechanical squeezing out of the resilient bodies also drives out filaments of slime, phlegm and mucous and turbid components which then either block the fluid-permeable partition wall, in so far as it is practically realised as a filter, or however pass through the partition wall, to the extent that it is apertured, into the saliva collecting vessel so that a clear salival fluid is no longer present.

The salival fluid must then be separated, for example by renewed filtering or centrifuging from the solid components which hinder or prevent further analysis. The press device is a complicated and expensive piece of apparatus and must therefore be used many times which gives rise to the dangers of lack of sterility and confusion (for example of the samples from different patients becoming confused).

The principal object of the present invention is thus to provide a method of the initially named kind in which a clear salival liquid which is free of all solid components is obtained in one working step from the resilient body full of saliva and can be used for analysis without further cleaning, filtering or centrifuging steps.

In order to satisfy this object the invention provides that the resilient body is arranged on an intermediate floor of a centrifuge tubule, with the intermediate floor forming the partition wall and being permeable to liquid and that the saliva is subsequently spun out by centrifuging into the lower part of the centrifuge tubule which forms the saliva collecting vessel.

As a result of the salival liquid being centrifuged out of the resilient body solid components and mucous filaments are better retained in the pores of the resilient body than is the case with vigorous and powerful mechanical squeezing out of the resilient body. For this reason contamination only passes through the floor into the lower part of the centrifuge tubule which forms the saliva collecting vessel to a small degree during centrifuging, and indeed even if the floor is not constructed as a filter but is instead apertured. In particularly advantageous manner these small amounts of contamination which have still managed to pass into the lower part of the centrifuge tubule together with the clear salival fluid are however also centrifuged out during the centrifuging process used to empty of the resilient body. In other words any contamination passing through the floor onto the lower part of the centrifuge tubule will collect at the base of the centrifuge tubule during centrifuging and, after termination of the centrifuging process only clear liquid saliva is present above the contamination which has been centrifuged out. This saliva can then be poured off after extracting the resilient body and passed on further use.

As, using the method of the invention, it is possible to operate with relatively small, inexpensively modified or adapted centrifuge tubules the apparatus used for carring out the method can be constructed as a throw away disposable unit which is packaged in sterile form, whereby both the danger of saliva samples being confused and also the danger of lack of sterility are effectively avoided, quite apart from the considerable saving in time which is obtained by simultaneous spinning out and centrifuging of the saliva samples. In particular, the invention avoids the transfer of the extracted saliva sample from a collecting vessel into a centrifuge tubule, which requires a lot of time and also brings about the danger of confusion.

A first embodiment of the method of the invention is characterised in that after the saliva has been centrifuged out the resilient body is taken out of the centrifuge tubule and the saliva which has been centrifuged out is subsequently poured out of the centrifuge tubule through the correspondingly apertured intermediate floor.

A particularly preferred embodiment is however characterised in that the resilient body full of saliva is arranged in a tube insert provided with a base or floor permeable to liquid which forms the partition wall; in that the tubular insert is arranged in the centrifuge tubule in such a way that the floor of the tubular insert has a substantial distance from the base of the centrifuge tubule; in that centrifuging subsequently takes place; and in that after centrifuging the tubular insert with the base arranged thereon is first taken out of the centrifuge tubule and the spun off saliva is then tipped out of the centrifuge tubule.

In this way, on removing the tubular insert the liquid permeable floor is also removed at the same time so that the clear liquid saliva can subsequently be tipped out in a particularly problem free manner.

A first advantageous apparatus for carrying out the method of the invention is characterised in that it includes a centrifuge tubule which has an apertured floor which extends over the full cross-section and which has a substantial spacing from the base of the centrifuge tubule and from its upper opening.

Although a filter could basically be arranged on the apertured floor, the use of the method of the invention results, even when using only an apertured floor, in only a small amount of contamination passing into the lower part of the centrifuge tubule. This contamination is however separated off from the clear liquid saliva during the centrifuging process.

An advantageous constructional embodiment of the invention is characterised in that it includes a centrifuge tubule and a tubular insert, the tubular insert having an external shape complementary to the upper internal region of the centrifuge tubule and a radially outwardly projecting annular flange in its upper region which, when the tubular insert is inserted into the centrifuge tubule, contacts the upper rim of the centrifuge tubule and also holds the tubular insert, even against the later occurring cetrifugal forces, with its liquid permeable floor at a substantial spacing from the base of the centrifuge tubule.

This arrangement is in particular such that the floor has a hole which is relatively large but is however sufficiently small that the resilient body arranged in the tubular insert is still held away from the base during centrifuging.

The annular flange ensures that the centrifugal forces which occur during centrifuging are transferred without problem and uniformly to the insert.

In order to make the handling of the centrifuge tubule in the centrifuge particularly simple, and to take account of the standardised dimensions which are provided there, the annular flange is arranged, in accordance with a further embodiment, so that it does not extend in the radial direction beyond the outer periphery of the centrifuge tubule.

In advantageous manner provision is also made that a cylindrical portion adjoins the top of the annular flange with the outer wall of the cylindrical portion being flush with the outer wall of the centrifuge tubule when the tubular insert is inserted into the centrifuge tubule.

With this arrangement it is expedient if a plug or stopper is inserted into the cylindrical portion, with the outer wall of the plug not projecting in the radial direction beyond the outer wall of the centrifuge tubule and preferably being likewise flush with the latter.

In this manner an overall assembly is obtained after inserting the tubular insert and after fitting the plug, in which no parts project in the radially outer directon beyond the outer periphery of the centrifuge tubule.

A preferred arrangement of the floor which forms the liquid permeable partition wall is characterised in that the floor is located at a distance of 40 to 60% and in particular of approxmately 50% of the height of the centrifuge tubule from its base.

A further advantageous embodiment is so constructed that the base of the centrifuge tubule is provided with a recess having a substantially smaller diameter than the lower portion of the centrifuge tubule, and with the recess preferably tapering in a downward direction.

The packed together salival filaments which do still pass into the lower part of the centrifuge tubule collect in the recess during centrifuging. In order to favour the retention of these salival filaments the floor of the centrifuge tubule should be provided with a very rough surface, in particular in the region of the recess.

The closability of the tubular insert by a plug ensures a reliable transport of the saliva impregnated resilient body up to the centrifuge.

A particular advantage of the invention resides in the fact that use of the tubular insert for the method of the invention means that standard centrifuge tubules can be used.

Figure 2:
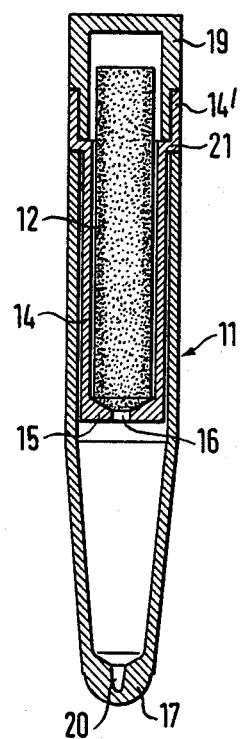
Figure 3:
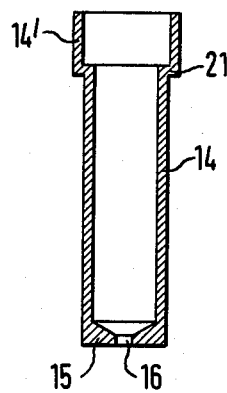
Figure 4:
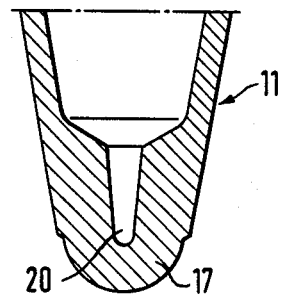

The invention will now be described in the following by way of example with reference to the drawing in which there is shown:

FIG. 1 a longitudinal-section of a first embodiment of a centrifuge tubule suitable for carrying out the method of the invention, FIG. 2 a corresopnding longitudinal-section of a further embodiment of an apparatus for carrying out the method of the invention in which a standard centrifuge tubule can be used, FIG. 3 a detailed sectional illustration of the tubular insert of the apparatus of FIG. 2, and FIG. 4 an enlarged sectional representation of the base region of the centrifuge tubule of FIG. 2.

As seen in FIG. 1 a centrifuge tubule 11 which is closed at the top by means of a plug 19 has an apertured intermediate floor 13 spaced by approximately 40% of the length of the centrifuge tubule from the base 27. An absorbent elastic body of inert material and of cylindrical shape is arranged on the intermediate floor 13. The body 12 is chewed by a patient until it has sucked itself full of saliva.

The body 12 which has sucked itself full of saliva is taken out of the mouth, is introduced into the centrifuge tubule 11 in the manner evident from FIG. 1 whereupon the plug or stopper 19 is pressed into the upper part of the centrifuge tubule 11. The saliva sample can now be conveyed to a laboratory where the centrifuging of the saliva out of the body 12 then takes place in a centrifuge. As a result of the constrution of the centrifuge tubule 11 in accordance with the invention the body 12 which is sucked full of saliva is also stored reliably, even during transport, and there is in particular no danger of different saliva samples becoming confused, because the centrifuge tubule 11 containing the body 12 can itself, in distinction to the moist resilient body 12, readily be labelled or provided with a stick on label.

During centrifuging the clear saliva passes through the apertured floor 13 to the base 17 of the centrifuge tubule 11. Should contamination still pass through the floor 13 then this will be spun out during centrifuging in the same working step and collects at the floor 17.

After centrifuging is completed the stopper 19 is pulled off and the resilient body 12 is removed from the upper part of the centrifuge tubule 11, for example with a pincette. The clear saliva can then be tipped out during which it flows through the holes of the floor 13. Any contamination which has been spun away remains at the base 17 of the centrifuge tubule 11.

As seen in FIGS. 2 and 3 the cylindrical resilient body 12 is accommodated in a tubular insert 14 which has a cylindrical outer shape complementary to the internal space of the upper part of the centrifuge tubule 11. The tubular insert is just sufficiently long that it only extends into the upper half of the centrifuge tubule 11, which is preferably of right-cylindrical shape, while the bottom part of the centrifuge tubule 11 tapers towards its base 17.

In order that the tubular insert 14 is reliably secured in the centrifuging position of FIG. 2 it has a radially outwardly projecting annular flange 21 in its upper region which is flush at its radially outer side with the outer wall of the centrifuge tubule 11 and which lies on the upper edge of the centrifuge tubule 11. A cylindrical portion 14' which is of the same shape as the upper part of the centrifuge tubule 11 adjoins the top of the tubular insert. A plug or stopper 19 is pressed into the cylindrical portion 14 and is likewise flush with the outer wall of the centrifuge tubule 11.

A bore 16 is formed at the center of the floor 15 of the tubular insert 14, the diameter of this bore is however substantially smaller than the diameter of the resilient body 12 accommodated in the tubular insert 14. The resilient body 12 itself almost fills the internal space of the tubular insert 14. In the upward direction the resilient body 12 can project up to and beyond the cylindrical portion 14', provided the plug 19 is of concave shape in the manner which is evident from FIG. 2 and providing the plug 19 can be sealingly pressed around the upper end of the body 12 into the cylindrical portion 14'.

As seen in FIGS. 2 and 4 a downwardly tapering recess 20 is provided in the base 17 of the centrifuge tubule 11, with the diameter of the recess 20 being substantially smaller than the diameter of the centrifuge tubule 11 at the lower end of the centrifuge tubule. The downwardly tapering recess 20 is sufficiently long that the saliva filaments and contamination which manage to pass into the lower part of the centrifuge tubule 11 can collect there in compacted, balled together form.

The embodiment of FIGS. 2 to 4 is particularly advantageous in that standard centrifuge tubules 11 can be used. The patients can chew the absorbent resilient body 12 at the doctor's surgery or at home and can subsequently insert it into a tubular insert which is available there and which is subsequently closed with the plug 19. Labelling can now be applied to the plug or to the tubular insert, quoting for example the name of the patient or the time at which the sample was taken. The tubular insert 14 filled with the sucked full body can now be conveyed to the laboratory without the danger of confusion occurring or without danger of the resilient body 12 being contaminated. In the laboratory the various tubular inserts which arrive there and which are provided with sucked full bodies are inserted into standard centrifuge tubules 11, which are however specially adapted to the requirements of the invention in so far as they have the recess which converges to a point in the base 17.

During the subsequent centrifuging process the clear saliva is driven through the opening 16 and collects on and above the base 17 of the centrifuge tubule 11. Any contamination and saliva filaments which may still emerge with the saliva ball together during centrifuging and are pressed into the downwardly converging recess 20 where they are so locked together and pressed solid that after termination of the centrifuging process, after removal of the tubular insert 14 from the centrifuge tubule 11, and after the tipping out of the clear saliva which has been centrifuged off, the contamination and saliva filaments are retained particularly well in the region of the base 17 of the centrifuge tubule 11.

The resilient body 12 can be a sponge, a foam material or a cellular material.

The tubular insert 14 and the associated plug 19 consist of a material which is only to be used once, so that they are thrown away after use. This is of importantness for reasons of hygiene.

It is a particularly favourable feature of the apparatus of the invention that the use of suction devices to remove the clear saliva which has been centrifuged off can be avoided.

We claim:

1. A method of extracting human saliva comprising the steps of: introducing one chewable, absorbent and resilient inert body into the mouth of a human being, having the body chewed by the human being until the body has sucked itself full of saliva, taking the body of saliva out of the mouth, placing the resilient body on a partition of a centrifuge tubule, said partition having at least one hole sufficiently large to allow passage therethrough of clear saliva and of contaminations thereof, and centrifuging the saliva out of the resilient body held in place by the partition, through the at least one hole of the partition into a lower part of the centrifugal tubule, which forms a saliva containing vessel, with contaminations settling in a lowermost portion of said part.

2. A method according to claim 1, comprising removing the resilient body from the centrifuge tubule after the saliva has been centrifuged out, and pouring the saliva which has been centrifuged out, out of the centrifuge tubule through the at least one hole in the partition.

3. A method according to claim 1, wherein the partition forms a lower portion of a tubular insert, comprising the steps of: arranging the tubular insert in the centrifuge tubule in such a way that the partition has a substantial distance from the base of the centrifuge tubule, and after centrifuging taking out the tubular insert with the partition from the centrifuge tubule, and tipping the spun off saliva out of the centrifuge tubule.

* * * * *